United States Patent
Tan et al.

(10) Patent No.: US 8,692,000 B2
(45) Date of Patent: Apr. 8, 2014

(54) PHASE TRANSFER CATALYSTS

(75) Inventors: Choon Hong Tan, Singapore (SG); Kuo Wei Huang, Jeddah (SA); Ting Ma, Singapore (SG); Xiao Fu, Singapore (SG)

(73) Assignee: National University of Singapore, Singapore (SG)

( * ) Notice: Subject to any disclaimer, the term of this patent is extended or adjusted under 35 U.S.C. 154(b) by 0 days.

(21) Appl. No.: 13/881,819

(22) PCT Filed: Oct. 27, 2011

(86) PCT No.: PCT/SG2011/000378
§ 371 (c)(1), (2), (4) Date: Apr. 26, 2013

(87) PCT Pub. No.: WO2012/057709
PCT Pub. Date: May 3, 2012

(65) Prior Publication Data
US 2013/0217889 A1    Aug. 22, 2013

Related U.S. Application Data

(60) Provisional application No. 61/407,499, filed on Oct. 28, 2010.

(51) Int. Cl.
*C07D 403/12* (2006.01)
*C07C 229/02* (2006.01)

(52) U.S. Cl.
USPC .......................... 548/312.7; 560/35

(58) Field of Classification Search
USPC .......................... 560/35; 548/312.7
See application file for complete search history.

(56) References Cited

PUBLICATIONS

Hellrung, Bruno. 87. Polarographische und voltammetrische Untersuchungen an symmetrischen Methin-, Azamethin- und Phosphamethincyaninen in Acetonitril. Helvetica Chimica Acta. 67(3), (1984), 770-773.*

* cited by examiner

*Primary Examiner* — Samantha Shterengarts
(74) *Attorney, Agent, or Firm* — Cesari and McKenna, LLP

(57) ABSTRACT

Compounds of formula (I): wherein $R_1$ to $R_8$, and $X^-$ are defined herein. Also disclosed are methods of making and using these compounds.

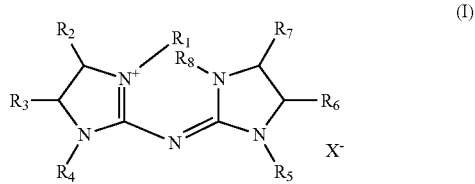

20 Claims, No Drawings

PHASE TRANSFER CATALYSTS

CROSS REFERENCE TO RELATED APPLICATION

This application is the national phase under 35 USC 371 of international application no. PCT/SG2011/000378, filed Oct. 27, 2011, which claims the benefit of the priority date of U.S. Patent application No. 61/407,499, filed Oct. 28, 2010. The contents of the aforementioned applications are incorporated herein in their entirety.

BACKGROUND

Asymmetric phase transfer catalysis has been recognized as a convenient and powerful methodology in organic chemistry. This synthetic approach provides many advantages, including simple procedure, mild conditions, suitability for large scale reactions, and safety.

Various chiral phase transfer catalysts have been developed in the past thirty years, e.g., N-alkylated cinchomimium halide and N-spiro chiral ammonium salt. See O'Donnell et al., J. Am. Chem. Soc., 1989, 111, 2353; Ooi et al., J. Am. Chem. Soc., 1999, 121, 6519.

Yet, there is a need for less expensive and more efficient chiral phase transfer catalysts.

SUMMARY

This invention is based on the discovery that certain pentanidium compounds can be used as chiral phase transfer catalysts. The term "pentanidium compounds" herein refers to alkylated or arylated salts of pentanidines that contain five nitrogen atoms in conjugation.

In one aspect, this invention features pentanidium compounds of formula (I):

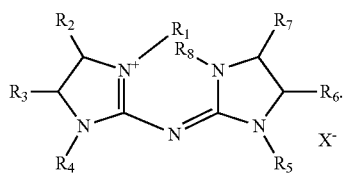

(I)

In this formula, each of $R_1$ and $R_8$, independently, is $C_1$-$C_{10}$ alkyl, $C_3$-$C_{20}$ cycloalkyl, $C_3$-$C_{20}$ heterocycloalkyl, aryl, or heteroaryl; or $R_1$ and $R_8$ form $C_1$-$C_{10}$ alkyl, $C_3$-$C_{20}$ cycloalkyl, $C_3$-$C_{20}$ heterocycloalkyl, aryl, or heteroaryl; each of $R_2$, $R_3$, $R_6$, and $R_7$, independently, is H, $C_1$-$C_{10}$ alkyl, $C_3$-$C_{20}$ cycloalkyl, $C_3$-$C_{20}$ heterocycloalkyl, aryl, or heteroaryl; or $R_2$ and $R_3$, together with the two carbon atoms to which they are attached, form $C_4$-$C_{20}$ cycloalkyl, $C_4$-$C_{20}$ heterocycloalkyl, aryl, or heteroaryl; or $R_6$ and $R_7$, together with the two carbon atoms to which they are attached, form $C_4$-$C_{20}$ cycloalkyl, $C_4$-$C_{20}$ heterocycloalkyl, aryl, or heteroaryl; each of $R_4$ and $R_5$, independently, is $C_1$-$C_{10}$ alkyl, $C_3$-$C_{20}$ cycloalkyl, $C_3$-$C_{20}$ heterocycloalkyl, aryl, or heteroaryl; $X^-$ is a halide ion, a hydroxide ion, a tetrafluoroboric acid ion, a nitric acid anion, a hexaflorophosphoric acid ion, a tetrakis(3,5-bis(trifluoromethyl)phenyl)borate, a sulfuric acid anion, a phosphoric acid anion, a citric acid anion, a methanesulfonic acid anion, a trifluoroacetic acid anion, a malic acid anion, a tartaric acid anion, a fumaric acid anion, a glutamic acid anion, a glucuronic acid anion, a lactic acid anion, a glutaric acid anion, a maleic acid anion, an acetic acid anion, or a p-toluenesulfonic acid ion; and at least one of the four carbon atoms to which $R_2$, $R_3$, $R_6$, and $R_7$ are attached has an R or S configuration.

One subset of the above-described compounds are those in which $R_1$ is identical to $R_8$, $R_2$ is identical to $R_7$, $R_3$ is identical to $R_6$, and $R_4$ is identical to $R_5$. In these compounds, all the carbon atoms to which $R_2$, $R_3$, $R_6$, and $R_7$ are attached have an R or S configuration (e.g., all of them having an R configuration, or all of them having a S configuration); each of $R_2$, $R_3$, $R_6$, and $R_7$, independently, is aryl or heteroaryl, or $R_2$ and $R_3$, together with the two carbon atoms to which they are attached, form $C_4$-$C_{20}$ cycloalkyl, and $R_6$ and $R_7$, together with the two carbon atoms to which they are attached, form $C_4$-$C_{20}$ cycloalkyl; and each of $R_1$, $R_4$, $R_5$, and $R_8$, independently, is $C_1$-$C_{10}$ alkyl.

Another subset of the compounds described above are those in which $R_1$ is identical to $R_8$, each of $R_2$ and $R_7$ is H, and $R_4$ is identical to $R_5$; all the carbon atoms to which $R_3$ and $R_6$ are attached have an R or S configuration; each of $R_3$ and $R_6$, independently, is aryl or heteroaryl; and each of $R_1$, $R_4$, $R_5$, and $R_8$, independently, is $C_1$-$C_{10}$ alkyl.

Still another subset of the compounds described above are those in which $R_1$ is identical to $R_8$, each of $R_3$ and $R_6$ is H, and $R_4$ is identical to $R_5$; all the carbon atoms to which $R_2$ and $R_7$ are attached have an R or S configuration; each of $R_2$ and $R_7$, independently, is aryl or heteroaryl; and each of $R_1$, $R_4$, $R_5$, and $R_8$, independently, is $C_1$-$C_{10}$ alkyl.

The term "alkyl" refers to a saturated hydrocarbon moiety, either linear or branched. The term "cycloalkyl" refers to a saturated, cyclic hydrocarbon moiety, such as cyclohexyl. The term "heterocycloalkyl" refers to a saturated, cyclic moiety having at least one ring heteroatom (e.g., N, O, or S), such as 4-tetrahydropyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, cycloalkyl, heterocycloalkyl, aryl, and heteroaryl mentioned herein include both substituted and unsubstituted moieties, unless specified otherwise. Possible substituents on cycloalkyl, heterocycloalkyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ diallcylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylic ester. On the other hand, possible substituents on alkyl include all of the above-recited substituents except $C_1$-$C_{10}$ alkyl. Cycloalkyl, heterocycloalkyl, aryl, and heteroaryl can also be fused with each other.

In another aspect, this invention features a method of preparing pentanidium compounds of formula (I) shown above.

The method includes reacting a compound of formula (II) with a compound of formula (III). The two formulae are shown below:

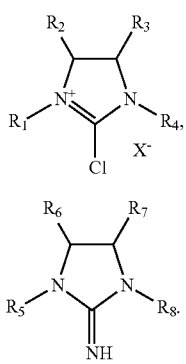

In formulae (II) and (III), $R_1$ to $R_8$, and $X^-$ are defined above. Also, at least one of the four carbon atoms to which $R_2$, $R_3$, $R_6$, and $R_7$ are attached has an R or S configuration.

In still another aspect, this invention features a method of preparing a chiral compound of formula (IV):

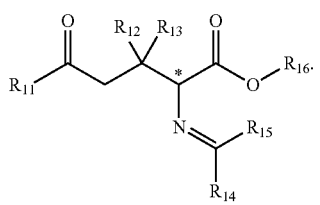

This method includes reacting an enone of formula (V):

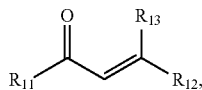

with a Schiff base of formula (VI):

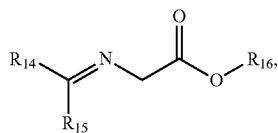

in the presence of a catalyst, which is a compound of formula (I) shown above.

In formulae (IV), (V), and (VI), $R_{11}$ is H, $C_1$-$C_{10}$ alkyl, $C_3$-$C_{20}$ cycloalkyl, $C_3$-$C_{20}$ heterocycloalkyl, aryl, or heteroaryl; each of $R_{12}$ and $R_{13}$, independently, is H, $C_1$-$C_{10}$ alkyl, $C_3$-$C_{20}$ cycloalkyl, $C_3$-$C_{20}$ heterocycloalkyl, aryl, or heteroaryl; or $R_{12}$ and $R_{13}$, together with the carbon atom to which they are attached, is $C_3$-$C_{20}$ cycloalkyl, or $C_3$-$C_{20}$ heterocycloalkyl; each of $R_{14}$ and $R_{15}$, independently, is H, $C_1$-$C_{10}$ alkyl, $C_3$-$C_{20}$ cycloalkyl, $C_3$-$C_{20}$ heterocycloalkyl, aryl, or heteroaryl; or $R_{14}$ and $R_{15}$, together with the carbon atom to which they are attached, is $C_3$-$C_{20}$ cycloalkyl, or $C_3$-$C_{20}$ heterocycloalkyl; $R_{16}$ is $C_1$-$C_{10}$ alkyl, $C_3$-$C_{20}$ cycloalkyl, $C_3$-$C_{20}$ heterocycloalkyl, aryl, or heteroaryl.

The details of one or more embodiments of the invention are set forth in the description below. Other features, objects, and advantages of the invention will be apparent from the description and also from the claims.

DETAILED DESCRIPTION

The pentanidium compounds of this invention can be prepared by methods well known in the art, e.g., Ma et al., J. Am. Chem. Soc., 2011, 133, 2828. The route shown in Scheme 1 below exemplifies synthesis of these compounds.

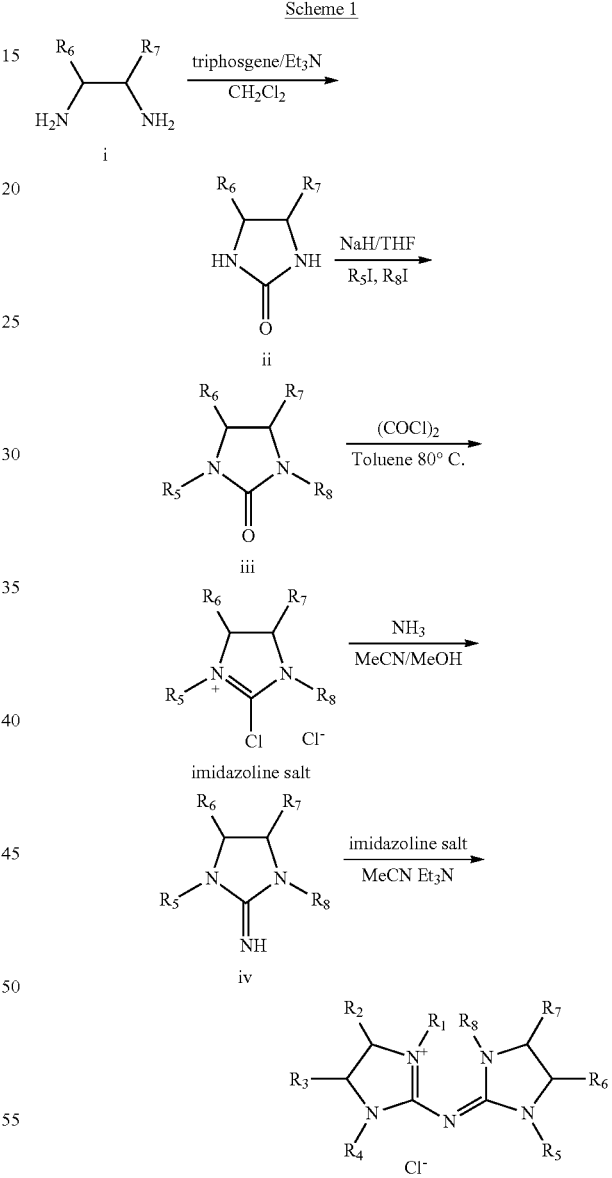

Specifically, a diamine compound i can react with triphosgene in the presence of a base to form compound ii, which can be converted into compound iii through alkylation. Compound iii can be treated with oxalyl chloride under a heating condition to yield an imidazoline salt. This salt can react with ammonia to obtain imidazolidin-2-imine iv, which in turn is treated with an imidzaoline salt to form the compounds of the invention, e.g., Compound 1a-1f shown below:

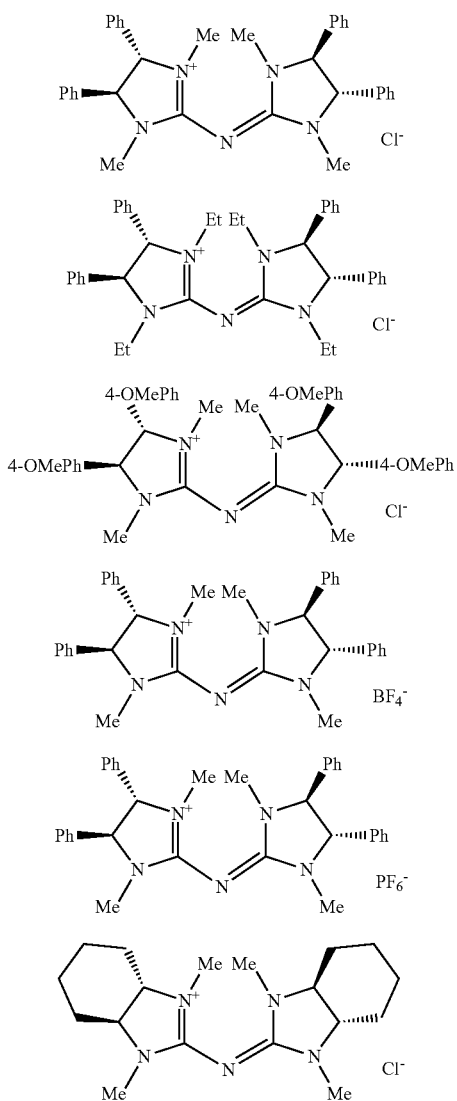

A pentanidium compound thus synthesized can be purified by any suitable method, such as column chromatography, high-pressure liquid chromatography, or recrystallization.

Other pentanidium compounds of this invention can be prepared using other suitable starting materials through the above-described synthetic routes and others known in the art. The methods set forth above may also additionally include steps to add or remove suitable protecting groups in order to ultimately allow synthesis of the pentanidium compounds. In addition, various synthetic steps may be performed in an alternate sequence or order to give the desired compounds. Synthetic chemistry transformations and protecting group methodologies (protection and deprotection) useful in synthesizing applicable pentanidium compounds are known in the art and include, for example, those described in R. Larock, *Comprehensive Organic Transformations*, VCH Publishers (1989); T. W. Greene and P. G. M. Wuts, *Protective Groups in Organic Synthesis,* 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

The pentanidium compounds described herein may contain a non-aromatic double bond and one or more asymmetric centers. Thus, they can occur as single enantiomers, individual diastereomers, diastereomeric mixtures, and cis- or trans-isomeric forms. All such isomeric forms are contemplated.

Also within the scope of this invention is a method of preparing the pentanidium compounds described above.

These pentanidium compounds can be used as chiral phase transfer catalysts in asymmetric reactions, such as asymmetric alkylation, Michael addition, aldol reaction.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

General Information $^{1}$H and $^{13}$C NMR spectra were recorded on a Bruker ACF300 (300 MHz), Bruker DPX300 (300 MHz), 500 MHz Bruker DRX NMR spectrometer, or AMX500 (500 MHz) spectrometer. Chemical shifts were reported in parts per million (ppm). The residual solvent peak was used as an internal reference. Low resolution mass spectra were obtained on a Finnigan/MAT LCQ spectrometer in ESI mode. High resolution mass spectra were obtained on a Finnigan/MAT 95XL-T spectrometer. Enantiomeric excess values were determined by chiral HPLC analysis on Dionex Ultimate 3000 HPLC units, including a Ultimate 3000 Pump, Ultimate 3000 variable Detectors. Optical rotations were recorded on a Jasco DIP-1000 polarimeter with a sodium lamp of wavelength 589 nm and reported as follows; T °Cλ [α] (c=g/100 mL, solvent). Melting points were determined on a BÜCHI B-540 melting point apparatus. Flash chromatography separations were performed on Merck 60 (0.040-0.063 mm) mesh silica gel. Toluene was distilled from sodium/benzophenone and stored under $N_2$ atmosphere. MeCN was dried by Molecular Sieve. Dichloromethane was distilled from $CaH_2$ and stored under $N_2$ atmosphere. Other reagents and solvents were commercial grade and were used as supplied without further purification, unless otherwise stated. Experiments involving moisture and/or air sensitive components were performed under a positive pressure of nitrogen in oven-dried glassware equipped with a rubber septum inlet. Reactions requiring temperatures −20 ° C. were stirred in either Thermo Neslab CB-60 with Cryotrol temperature controller or Eyela PSL-1400 with digital temperature controller cryobaths. Isopropanol was used as the bath medium. All experiments were monitored by analytical thin layer chromatography (TLC). Instrumentations Proton nuclear magnetic resonance ($^{1}$H NMR), carbon NMR ($^{13}$C NMR), phosphorous NMR ($^{31}$P NMR), and fluorine NMR ($^{19}$F NMR) spectra were recorded in $CDCl_3$ otherwise stated. $^{1}$H (500.1331 MHz), $^{13}$C (125.7710 MHz) with complete proton decoupling, $^{31}$P (121 MHz) with complete proton decoupling, and $^{1}$H NOESY NMRs were performed on a 500 MHz Bruker DRX NMR spectrometer. $^{19}$F NMR (282.3761 MHz) was performed on a 300 MHz Bruker ACF spectrometer. All compounds synthesized were stored in a −34° C. freezer.

Example 1

Synthesis of Compound 1a:
(S,S)-Tetraphenyl-tetramethyl-pentanidium chloride

Provided below are the scheme and detailed procedures for synthesizing intermediates (Compounds B-D) and Compound 1a from Compound A.

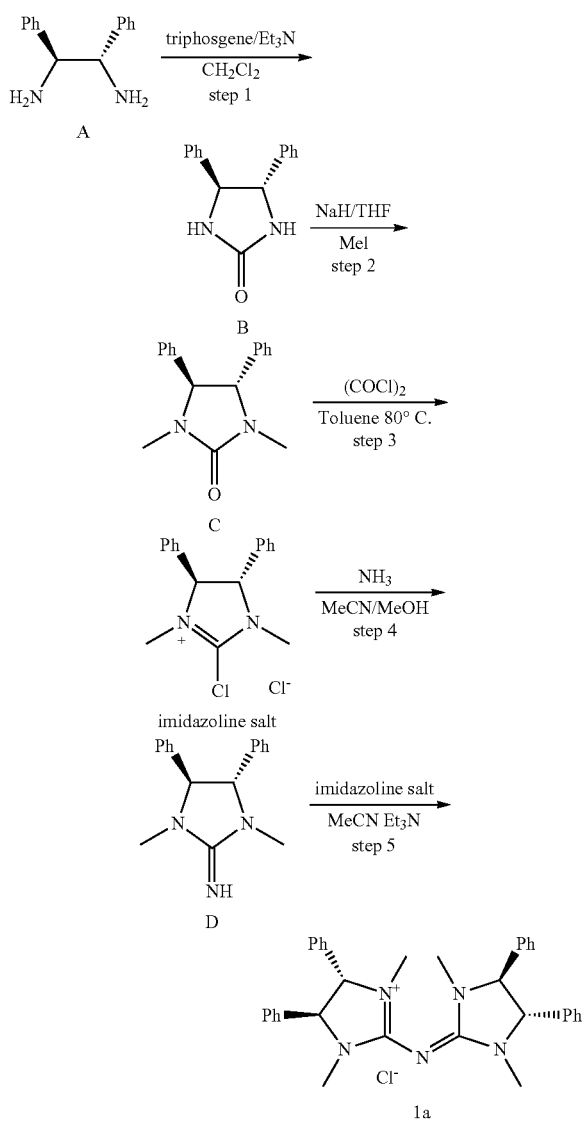

Step 1. Synthesis of (S,S)-4,5-Diphenylimidazolidin-2-one (Compound B)

To a solution of Compound A, a chiral diamine (2.12 g, 10 mmol) and Et$_3$N (4.1 ml, 30 mmol) in CH$_2$Cl$_2$ (25 mL), was added triphosgene (977 mg, 3.3 mmol, dissolved in 5 mL CH$_2$Cl$_2$) in a dropwise manner, keeping the temperature lower than 5° C. all the time. After allowing the temperature to rise to room temperature, an additional 4-5 hours of stirring was required to allow the reaction to complete (monitored by TLC). After diamine A was completely consumed, reaction was quenched by water (20 mL) and extracted using CH$_2$Cl$_2$ 3 times (30 mL×3). The combined organic layer was washed by brine and dried by Na$_2$SO$_4$. Solvent was removed under reduced pressure. Compound B was pale yellow solid, which can be used in the next step without any further purification. $^1$H NMR (300 MHz, CDCl$_3$): δ 7.38-7.34 (m, 6H), 7.27-7.30 (m, 4H), 5.83 (s, 2H), 4.57 (s, 2H). $^{13}$C NMR (126 MHz, CDCl$_3$) δ 163.1, 140.2, 128.7, 128.2, 126.4, 65.9; LRMS (ESI) m/z 239.1 (M+H$^+$), HRMS (ESI) m/z 239.1185 ([M+H$^+$]), calc. for [C$_{15}$H$_{14}$N$_2$O+H$^+$]239.1179.

Step 2. Synthesis of (S,S)-1,3-Dimethyl-4,5-diphenylimidazolidin-2-one (Compound C)

To a suspension of NaH (720 mg, 30 mmol, 3.0 equiv) in THF (15 mL) was added a solution of Compound B (from step 1) in THF (20 mL). After 0.5 h, 2.3 mL of MeI (37 mmol, 3.7 equiv) was added in one portion. Upon completion of the reaction (monitored by TLC), the mixture was filtered through a short pad of Celite. Solvent was removed under reduced pressure and Compound C was obtained by flash chromatography (silica gel, hexane-ethyl acetate 3:1), as a white solid, 2.10 g (2 steps, 80% overall yield). $^1$HNMR (300 MHz, CDCl$_3$): δ 7.34-7.32 (m, 6H), 7.14-7.11 (m, 4H), 4.07 (s, 2H), 2.69 (s, 6H); $^{13}$C NMR (126 MHz, CDCl$_3$) δ 161.7, 137.9, 128.7, 128.3, 127.2, 70.2, 29.9; LRMS (ESI) m/z 267.1 (M+H$^+$), HRMS (ESI) m/z 267.1497([M+H$^+$]), calc. for [C$_{17}$H$_{18}$N$_2$O +H$^+$]267.1492.

Step 3. Synthesis of Imidazoline Salt

A 100 mL RBF was charged with a solution of Compound C (1.60 g, 6 mmol, 1 equiv) in toluene (40 mL) with a condenser under N$_2$ atmosphere. (COCl)$_2$ (5.2 mL, 60 mmol, 10 equiv) was added via syringe in one portion. The mixture was refluxed overnight until C was completely reacted. Toluene was removed under reduced pressure and solid imidazoline salt (1.93 g) was obtained for the next step without any purification. Note that imidazoline salt is air and moisture sensitive, which should be stored under nitrogen atmosphere or vacuum.

Step 4. Synthesis of (4S,5S)-1,3-Dimethyl-4,5-diphenylimidazolidin-2-imine (Compound D)

Separate half of imidazoline salt for the step 5. The other part (960 mg) was dissolved in dry MeCN/MeOH (volume ratio 1:1, 20 mL), NH$_3$ was bubbled into the solution at 0° C. for 0.5 h. Then, the seal tube was sealed and placed in 60° C. oil bath. After stirring overnight to complete reaction, pressure was released and water was added (40 mL). The mixture was extracted by CH$_2$Cl$_2$ 3 times (20 mL×3). The combined organic layer was dried by Na$_2$SO$_4$. After removing solvent under reduced pressure, Compound D was obtained as a brown solid, 801 mg, >99% yield. $^1$H NMR (300 MHz, CDCl$_3$): δ 7.17-7.14 (m, 6H), 6.99-6.97 (m, 4H), 4.48 (b, 1H), 3.87 (s, 2H), 2.52 (s, 6H); $^{13}$C NMR (125.77 MHz, CDCl$_3$): δ 163.3, 137.9, 128.6, 128.2, 127.4, 72.1, 31.4; LRMS (ESI) m/z 266.1 (M+H$^+$), HRMS (ESI) m/z 266.1664 ([M+H$^+$]), calc. for [C$_{17}$H$_{19}$N$_3$+H$^+$]266.1652.

Step 5. Synthesis of (S,S)-Tetraphenyl-tetramethyl-pentanidium chloride (Compound 1a)

To a solution of Compound D (800 mg, 3.06 mmol) and Et$_3$N (0.45 mL, 3.24 mmol) in MeCN (15 mL) was added a solution of imidazoline salt (from step 4, 970 mg, 1.0 equiv) in dry MeCN (10 mL) in a dropwise manner. The reaction mixture was stirred until the reaction was completed. Reaction was quenched by water (20 mL), and extracted using CH$_2$Cl$_2$ 3 times (20 mL×3). The combined organic layer was dried by Na$_2$SO$_4$. Solvent was removed under reduced pressure. The brown solid obtained was re-crystallized by CH$_2$Cl$_2$/ethyl acetate solvent system. Compound 1a was isolated as a white solid, 820 mg, 48% yield. mp 276-278° C.; $^1$H NMR (500 MHz, CDCl$_3$): δ 7.35-7.34 (m, 12H), 7.24-7.21 (m, 8H), 4.67 (s, 4H), 2.93 (s, 12H); $^{13}$C NMR (126 MHz, CDCl$_3$) δ 159.5, 135.4, 129.3, 129.3, 127.6, 72.6, 32.5; LRMS (ESI) m/z 514.5 ([M−Cl$^-$]$^+$), HRMS (ESI) m/z 514.2970 ([M–Cl⁻])⁺, calc. for [C₃₄H₃₆N₅⁺]514.2965. [α]$_D^{29}$=+171.2 (c 1.18, CHCl₃).

Example 2

Synthesis of Compound 1b: (S,S)-Tetraphenyl-tetraethyl-pentanidium chloride

Compound 1b was prepared in a manner similar to that described in Example 1, with two additional steps described below. See Ryoda, A et al., JOC, 2008, 73, 133.

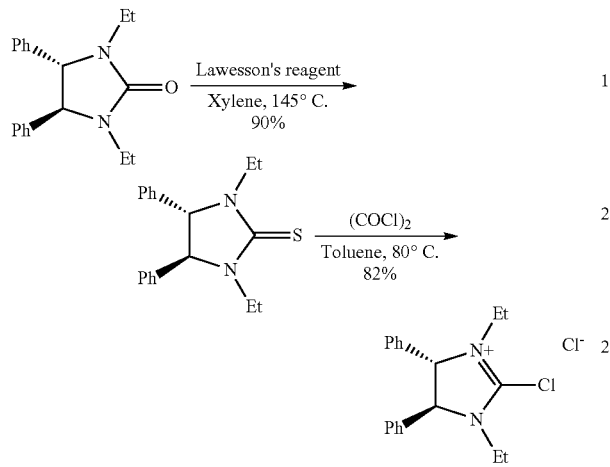

White solid. ¹H NMR (500 MHz, CDCl₃) δ 7.42-7.40 (m, 12H), 7.17-7.15 (m, 8H), 4.53 (s, 4H), 4.31-4.24 (m, 4H), 3.05-3.03 (m, 4H), 1.16 (t, J=7.5, 12H); ¹³C NMR (126 MHz, CDCl₃) δ 157.1, 136.5, 129.4, 129.4, 127.0, 69.8, 39.0, 11.3; LRMS (ESI) m/z 570.5 ([M—Cl⁻])⁺, HRMS (ESI) m/z 570.3586 ([M–Cl⁻])⁺, calc. for [C₃₈H₄₄N₅⁺] 570.3591.

Example 3

Synthesis of Compound 1c: (S,S)-Tetra-4-methoxy-phenyl-tetraethyl-pentanidium chloride Compound 1c was prepared in a manner similar to that described in Example 1 except that a different starting material, i.e., (1S,2S)-1,2-bis(4-methoxyphenyl)ethane-1,2-diamine, was used.

White solid; 56% yield. ¹H NMR (300 MHz, CDCl₃) δ 7.19 (d, J=8.7 Hz, 8H), 6.89 (d, J=8.7 Hz, 8H), 4.60 (s, 4H), 3.79 (s, 12H), 2.90 (s, 12H); ¹³C NMR (75 MHz, CDCl₃) δ 160.2, 159.2, 129.0, 127.3, 114.6, 72.2, 55.2, 32.3; LRMS (ESI) m/z 634.5 ([M–Cl⁻])⁺, HRMS (ESI) m/z 634.3403 ([M–Cl⁻])⁺, calc. for [C₃₈H₄₄N₅O₄⁺] 634.3388.

Example 4

Synthesis of Compound 1d: (S,S)-Tetraphenyl-tetramethyl-pentanidium tetrafluoroborate Compound 1d was synthesized by reacting Compound 1a (prepared in Example 1) with sodium tetrafluoroborate in the following manner:

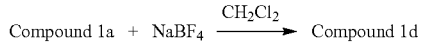

White solid; 98% yield. ¹H NMR (300 MHz, CDCl3) δ 7.40-7.37 (m, 12H), 7.26-7.22 (m, 8H), 4.62 (s, 4H), 2.91 (s, 12H); ¹³C NMR (75 MHz, CDCl3) δ 159.5, 135.5, 129.30, 129.2, 127.6, 104.9, 72.7, 32.2; ¹⁹F NMR (282 MHz, CDCl₃) δ-76.59.

Example 5

Synthesis of Compound 1e: (S,S)-Tetraphenyl-tetramethyl-pentanidium hexafluorophosphate Compound 1e was synthesized by reacting Compound 1a (prepared in Example 1) with sodium hexafluorophosphate in the following manner:

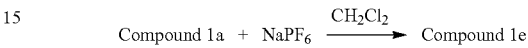

White solid; 99% yield. ¹H NMR (300 MHz, CDCl₃) δ 7.43-7.40 (m, 12H), 7.27-7.24 (m, 8H), 4.63 (s, 4H), 2.92 (s, 12H); ¹³C NMR (75 MHz, CDCl₃) δ 159.4, 135.4, 129.4, 129.3, 127.6, 72.7, 32.2; ¹⁹F NMR (282 MHz, CDCl₃) δ 3.32 (d, 710Hz). ³¹P NMR (121 MHz, CDCl₃) δ-143.6 (tt, J₁=709 Hz, 1418 Hz).

Example 6

Synthesis of Compound 1f: (S,S)-Dicyclohexyl-tetramethyl-pentanidium chloride

Compound 1f was prepared in a manner similar to that described in Example 1 except that a different starting material, i.e., (1S,2S)-cyclohexane-1,2-diamine, was used. Also, the compound thus-synthesized was purified by flash chromatography (silica gel, CH₂Cl₂/MeOH, 50:1).

Colorless oil. ¹H NMR (300 MHz, CDCl₃) δ 3.01-2.99 (m, 4H), 2.79 (s, 12H), 2.19-2.10 (m, 8H), 1.93 (d, J=6.2 Hz, 4H), 1.45-1.42 (m, 4H); ¹³C NMR (75 MHz, CDCl₃) δ 162.7, 66.2, 31.4, 27.8, 23.8; LRMS (ESI) m/z 318.5 ([M–Cl⁻])⁺, HRMS (ESI) m/z 318.2659 ([M–Cl⁻])⁺, calc. for [C₁₈H₃₂N₅⁺] 318.2652.

Example 7

Use of Compound 1a as a Chiral Phase Transfer Catalyst in Michael Addition 7-1. Synthesis of Compounds 4a-4f Table 1 below lists Michael addition of a Schiff Base (i.e., Compound 2) with various vinyl ketones and acrylates (i.e., Compounds 3a-3f) to yield Compounds 4a-4f in the presence of Compound 1a as the catalyst. Compounds 3a-3f were prepared following the procedures described in Ma et al., J. Am. Chem. Soc., 2011, 133, 2828.

TABLE 1

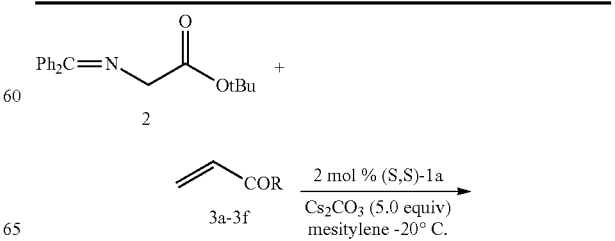

TABLE 1-continued $$Ph_2C=N \overset{H}{\underset{(CH_2)_2COR}{\bigg|}} \overset{O}{\underset{}{\overset{\|}{C}}}-OtBu$$

4a-4f

| Entry | 3 [R]      | 4  | Time (h) | Yield (%)[b] | ee (%)[c] |
|-------|------------|----|----------|--------------|-----------|
| 1     | 3a [Et]    | 4a | 4        | 92           | 93        |
| 2     | 3b [Me]    | 4b | 3        | 86           | 91        |
| 3     | 3c [n-Bu]  | 4c | 1        | 97           | 93        |
| 4     | 3d [Ph]    | 4d | 1        | 50           | 88        |
| 5     | 3e [OEt]   | 4e | 6        | 71           | 97        |
| 6     | 3f [OBn]   | 4f | 4        | 80           | 96        |
| 7[d]  | 3f [OBn]   | 4f | 6        | 77           | 93        |
| 8[e]  | 3f [OBn]   | 4f | 12       | 75           | 91        |

[a]Reactions were performed by using Compound 2 (0.06 mmol) and Compounds 3a-3f (0.12 mmol) in 0.6 ml mesitylene for indicated time.
[b]Yield of isolated product.
[c]Determined by HPLC analysis using a Chiralcel OD-H column.
[d]0.1 mol % of catalyst was used.
[e]0.03 mol % of catalyst was used.

Synthesis of (R)-tert-Butyl-2-((diphenylmethylene)amino)-5-oxoheptanoate (Compound 4a)

tert-Butyl glycinate benzophenone Schiff base, Compound 2 (17.7 mg, 0.06 mmol, 1.0 equiv), (S, S)-1a (0.66 mg, 0.0012 mmol, 0.02 equiv) and $Cs_2CO_3$ (97 mg, 0.2 mmol, 5.0 equiv) were placed in mesitylene (0.6 mL) and stirred at −20 °C. for 10 min, then ethyl vinyl keton 3a (12.8 μL, 0.12 mmol, 2.0 equiv) was added by syringe in one portion. The reaction mixture was stirred at −20° C. and monitored by TLC. After indicated time, upon complete consumption of 2, the reaction mixture was directly loaded onto a short silica gel column, followed by gradient elution with hexane/ethyl acetate (15/1-12/1 ratio). After removing the solvent, product 4a (20.9 mg, 92% yield) was obtained as colorless oil. $^1$H NMR (300 MHz, $CDCl_3$) δ 7.67-7.58 (m, 2H), 7.47-7.27 (m, 6H), 7.16 (dd, J=6.4, 3.1 Hz, 2H), 3.95 (t, J=6.1 Hz, 1H), 2.59-2.32 (m, 4H), 2.15 (dd, J=13.6, 7.6 Hz, 2H), 1.43 (s, 9H), 1.01 (t, J=7.3 Hz, 3H); $^{13}$C NMR (75 MHz, $CDCl_3$) δ 210.8, 170.9, 170.3, 139.4, 136.4, 130.2, 128.5, 127.9, 127.6, 81.0, 64.7, 38.4, 35.8, 27.8, 7.67; LRMS (ESI) m/z 402.1 (M+Na$^+$), HRMS (ESI) m/z 402.2037 ([M+Na$^+$]), calc. for [$C_{24}H_{29}NO_3$+Na$^+$] 402.2040; $[α]_D^{29}$=+72.8 (c 1.55, $CHCl_3$); HPLC analysis: Chiralcel OD-H (Hex/IPA=92/8, 0.8 mL/min, 230 nm, 23° C.), 5.9 (major), 8.0 min, 93% ee.

Synthesis of (R)-tert-Butyl-2-((diphenylmethylene)amino)-5-oxohexanoate (Compound 4b)

Colorless oil; 86% yield. $^1$H NMR (300 MHz, $CDCl_3$) δ 7.67-7.58 (m, 2H), 7.47-7.27 (m, 6H), 7.17-7.15 (m, 2H), 3.95 (t, J=6.1 Hz, 1H), 2.59-2.45 (m, 2H), 2.35-2.15 (m, 2H), 2.12 (s, 3H), 1.43 (s, 9H); $^{13}$C NMR (75 MHz, $CDCl_3$) δ 208.2, 170.9, 170.4, 139.4, 136.4, 130.2, 128.7, 128.5, 128.4, 128.4, 127.9, 127.6, 81.1, 64.6, 39.7, 29.8, 28.0, 27.7; LRMS (ESI) m/z 388.1 (M+Na$^+$), HRMS (ESI) m/z 388.1900 ([M+Na$^+$]), calc. for [$C_{23}H_{27}NO_3$+Na$^+$] 388.1883; $[α]_D^{29}$=+64.2 (c 1.30, $CHCl_3$); HPLC analysis: Chiralcel OD-H (Hex/IPA=92/8, 0.8 mL/min, 210 nm, 23°C.), 6.5 (major), 7.2 min, 91% ee.

Synthesis of (R)-tert-Butyl-2-((diphenylmethylene)amino)-5-oxononanoate (Compound 4c)

Colorless oil; 97% yield. $^1$H NMR (500 MHz, $CDCl_3$) δ 7.66-7.60 (m, 2H), 7.47-7.41 (m, 3H), 7.38-7.37 (m, 1H), 7.32 (t, J=7.5 Hz, 2H), 7.19-7.13 (m, 2H), 3.95 (t, J=12.1 Hz,1H), 2.55-2.42 (m, 2H), 2.41-2.33 (m, 2H), 2.14 (dd, J=13.8, 7.5 Hz, 2H), 1.54-1.47 (m, 2H), 1.43 (s, 9H), 1.27 (dd, J=15.0, 7.4 Hz, 2H), 0.88 (t, J=7.3 Hz, 3H); $^{13}$C NMR (75 MHz, $CDCl_3$) δ 210.6, 171.0, 170.3, 139.4, 136.4, 130.2, 128.7, 128.5, 128.4, 127.9, 127.6, 81.0, 64.7, 42.4, 38.8, 28.0, 27.7, 25.8, 22.2, 13.8; LRMS (ESI) m/z 430.1 (M+Na$^+$), HRMS (ESI) m/z 430.2364 ([M+Na$^+$]), calc. for [$C_{26}H_{33}NO_3$+Na$^+$] 430.2353; $[α]_D^{29}$=+43.4 (c 1.62, $CHCl_3$); HPLC analysis: Chiralcel OD-H+Chiralcel OD-H (Hex/IPA=95/5, 0.5 mL/min, 230 nm, 23° C.), 19.4 (major), 23.6 min, 93% ee.

Synthesis of (R)-tert-Butyl-2-((diphenylmethylene)amino)-5-oxo-5-phenyl pentanoate(Compound 4d)

Colorless oil; 50% yield. $^1$H NMR (300 MHz, $CDCl_3$) δ 7.95-7.93 (m, 2H), 7.65 (d, J=7.1 Hz, 2H), 7.56-7.53 (m, 1H), 7.45-7.39 (m, 6H), 7.32 (t, J=7.3 Hz, 2H), 7.15-7.13 (m, 2H), 4.08 (t, J=6.0 Hz, 1H), 3.16-3.01 (m, 2H), 2.33 (dd, J=13.3, 6.9 Hz, 2H), 1.45 (s, 9H);$^{13}$C NMR (75 MHz, $CDCl_3$) δ 199.6, 176.1, 171.0, 170.1, 136.8, 132.9, 132.4, 130.3, 130.0, 128.8, 128.5, 128.4, 128.2, 128.1, 128.0, 127.7, 64.7, 34.7, 28.0; LRMS (ESI) m/z 450.1 (M+Na$^+$), HRMS (ESI) m/z 450.2056 ([M+Na$^+$]), calc. for [$C_{28}H_{29}NO_3$+Na$^+$]450.2040; $[α]_D^{29}$=19.1 (c 0.5, $CHCl_3$); HPLC analysis: Chiralcel OD-H (Hex/IPA=92/8, 0.8 mL/min, 254 nm, 23° C.), 6.5 (major), 8.8 min, 88% ee.

Synthesis of (R)-1-tert-Butyl-5-ethyl-2-((diphenylmethylene)amino)pentanedioate (Compound 4e)

Colorless oil; 71% yield. $^1$H NMR (500 MHz, $CDCl_3$) δ 7.67-7.6 (m, 2H), 7.47-7.41 (m, 3H), 7.40-7.35 (m, 1H), 7.35-7.29 (m, 2H), 7.20-7.14 (m, 2H), 4.05 (q, J=7.1 Hz, 2H), 3.97 (dd, J=6.9, 5.7 Hz, 1H), 2.35 (dd, J=8.6, 6.8 Hz, 2H), 2.33-2.21 (m, 2H), 1.44 (s, 9H), 1.19 (t, J=7.1 Hz, 3H); $^{13}$C NMR (75 MHz, $CDCl_3$) δ 210.8, 170.9, 170.3, 139.4, 136.4, 130.2, 128-.5, 127.9, 127.6, 81.0, 64.7, 38.4, 35.8, 27.8, 7.67; LRMS (ESI) m/z 418.1 (M+Na$^+$), HRMS (ESI) m/z 418.1997 ([M+Na$^+$]), calc. for [$C_{24}H_{29}NO_4$+Na$^+$] 418.1989; $[α]_D^{29}$=+ 75.2 (c 1.38, $CHCl_3$); HPLC analysis: Chiralcel OD-H (Hex/IPA=95/5, 0.5 mL/min, 254 nm, 23° C.), 9.5 (major), 11.6 min, 97% ee.

Synthesis of (R)-5-Benzyl-1-tert-butyl-2-((diphenylmethylene)amino)pentanedioate (Compound 4f)

Colorless oil; 80% yield. $^1$H NMR (500 MHz, $CDCl_3$) δ 7.67-7.63 (m, 2H), 7.44-7.39 (m, 3H), 7.39-7.36 (m, 1H), 7.36-7.27 (m, 7H), 7.18-7.13 (m, 2H), 5.04 (s, 2H), 3.98 (dd, J=7.4, 5.2 Hz, 1H), 2.43 (dd, J=11.3, 5.2 Hz, 2H), 2.31-2.20 (m, 2H), 1.44 (s, 9H). $^{13}$C NMR (75 MHz, $CDCl_3$) δ 172.9, 170.7, 139.4, 136.4, 135.9, 130.2, 128.7, 128.5, 128.4, 128.3, 128.1, 127.9, 127.6, 81.1, 66.1, 64.8, 30.7, 28.5, 28.0; LRMS (ESI) m/z 480.1 (M +Na$^+$), HRMS (ESI) m/z 480.2165 ([M + Na$^+$]), calc. for [$C_{29}H_{31}NO_4$+Na$^+$] 480.2145; $[α]_D^{29}$=+57.5 (c 1.72, $CHCl_3$); HPLC analysis: Chiralpak AD-H+Chiralcel OD-H (Hex/IPA=92/8, 0.8 mL/min, 210 nm, 23° C.), 12.9 (major), 13.8 min, 96% ee.

7-2. Synthesis of Compounds 6a-6p

Table 2 below lists Michael addition of a Schiff Base (i.e., Compound 2) with various chalcones (i.e., Compounds 5a-5p) to yield Compounds 6a-6p in the presence of Compound 1a as the catalyst. Compounds 5a-5p were prepared following the procedures described in Ma et al., J. Am. Chem. Soc., 2011, 133, 2828.

TABLE 2

Ph₂C=N-CH₂-C(O)-OtBu (2)

+

R¹-C(O)-CH=CH-R² (5a-5p)

2 mol % (S,S)-1a
Cs₂CO₃ (5.0 equiv)
mesitylene -20° C.

→

R¹-C(O)-CH₂-CH(R²)-CH(NH=CPh₂)-CO₂tBu (2R,3S)
6a-6p Single diastereomer

| entry | R¹, R² | Product | Time (h) | Yield (%)[b] | ee (%)[c] |
|---|---|---|---|---|---|
| 1 | Ph, Ph | 6a | 12 | 98 | 92 |
| 2 | Ph, 1-naphthyl | 6b | 12 | 91 | 92 |
| 3 | Ph, 2-naphthyl | 6c | 24 | 93 | 90 |
| 4 | Ph, 4-PhC₆H₄ | 6d | 21 | 88 | 91 |
| 5 | Ph, 4-FC₆H₄ | 6e | 18 | 89 | 90 |
| 6 | Ph, 4-ClC₆H₄ | 6f | 15 | 98 | 92 |
| 7 | Ph, 4-BrC₆H₄ | 6g | 15 | 96 | 92 |
| 8 | Ph, 4-NO₂C₆H₄ | 6h | 10 | 91 | 94 |
| 9 | Ph, 2-ClC₆H₄ | 6i | 12 | 93 | 94 |
| 10 | Ph, 4-MeOC₆H₄ | 6j | 36 | 89 | 85 |
| 11 | 4-ClC₆H₄, Ph | 6k | 12 | 90 | 92 |
| 12 | 4-NO₂C₆H₄, Ph | 6l | 12 | 91 | 91 |
| 13 | 4-MeOC₆H₄, Ph | 6m | 18 | 83 | 87 |
| 14 | 2-naphthyl, Ph | 6n | 11 | 80 | 91 |
| 15 | 2-fural, Ph | 6o | 12 | 95 | 90 |
| 16 | 2-thiophenyl, Ph | 6p | 12 | 92 | 90 |
| 17[d] | Ph, 4-ClC₆H₄ | 6f | 24 | 89 | 92 |

[a] Reactions were performed by using Compound 2 (0.06 mmol) and Compounds 5a-5p (0.072 mmol) in 0.6 ml mesitylene for indicated time.
[b] Yield of isolated product.
[c] Determined by HPLC analysis using Chiralcel OD-H column. Only one diastereomer was observed, absolute configuration was verified by single crystal X-ray diffraction of 7.
[d] 2 (0.1 mmol), 5f (0.12 mmol) and 2.5 equiv Cs₂CO₃ was used with catalyst loading of 0.05 mol %.

Synthesis of (2R, 3S)-tert-Butyl 2-((diphenylmethylene)amino)-5-oxo-3,5-diphenylpentanoate (Compound 6a)

tert-Butyl glycinate benzophenone Schiff base 2 (17.7 mg, 0.06 mmol, 1.0 equiv), (S,S)-1a (0.66 mg, 0.0012 mmol, 0.02 equiv) and Cs₂CO₃ (97 mg, 0.2 mmol, 5.0 equiv) were placed in mesitylene (0.6 mL) and stirred at −20° C. for 10 min, followed by chalcone 5a (15.0 mg, 0.072 mmol, 1.2 equiv). The reaction mixture was stirred at −20° C. and monitored by TLC. After indicated time, upon complete consumption of 2, the reaction mixture was directly loaded onto a short silica gel column, followed by gradient elution with hexane/ethyl acetate (15/1-12/1 ratio). After removing the solvent, product 6a (29.6 mg, 98% yield) was obtained as colorless oil. $^1$H NMR (300 MHz, CDCl₃) δ 8.00-7.96 (m, 2H), 7.74-7.64 (m, 2H), 7.58-7.27 (m, 9H), 7.22-7.08 (m, 5H), 6.73 (d, J=6.4 Hz, 2H), 4.27-4.16 (m, 2H), 3.83-3.70 (m, 1H), 3.69-3.57 (m, 1H), 1.33 (s, 9H); $^{13}$C NMR (75 MHz, CDCl₃) δ 198.6, 171.0, 170.0, 141.3, 139.3, 137.2, 136.2, 132.7, 130.3, 128.8, 128.5, 128.4, 128.3, 128.1, 128.0, 127.9, 127.5, 126.5, 81.2, 70.9, 44.8, 40.0, 27.8; LRMS (ESI) m/z 526.1 (M+Na⁺), HRMS (ESI) m/z 526.2373 ([M+Na⁺]), calc. for [C₃₄H₃₃NO₃+Na⁺] 526.2353; [α]$_D^{29}$=+58.8 (c 2.48, CHCl₃); HPLC analysis: Chiralcel OD-H (Hex/IPA=95/5, 0.5 mL/min, 230 nm, 23° C.), 10.9 (major), 21.5 min, 92% ee.

(2R,3S)-tert-Butyl-2-((cliphenylmethylene)amino)-3-(naphthalen-1-yl)-5-oxo-5-phenylpentanoate (Compound 6b)

Colorless oil; 91% yield. $^1$H NMR (500 MHz, CDCl₃) δ 8.10 (d, J=8.2 Hz, 1H), 8.05-7.98 (m, 2H), 7.80 (d, J=7.6 Hz, 1H), 7.70-7.60 (m, 3H), 7.56-7.52 (m, 1H), 7.48-7.36 (m, 5H), 7.33 (t, J=7.4 Hz, 2H), 7.30-7.23 (m, 2H), 7.11 (t, J=7.4 Hz, 1H), 6.96 (t, J=7.4 Hz, 2H), 6.27 (s, 2H), 5.20-5.10 (m, 1H), 4.30 (d, J=3.7 Hz, 1H), 4.11 (dd, J=17.3, 9.8 Hz, 1H), 3.81 (dd, J=17.3, 4.2 Hz, 1H), 1.35 (s, 9H); $^{13}$C NMR (75 MHz, CDCl₃) δ 198.5, 171.1, 170.3, 139.3, 137.2, 135.8, 133.9, 132.7, 131.7, 130.2, 128.7, 128.5, 128.4, 128.1, 127.9, 127.7, 127.1, 126.9, 125.9, 125.2, 124.8, 123.0, 81.3, 69.2, 39.2, 27.8; LRMS (ESI) m/z 576.1 (M+Na⁺), HRMS (ESI) m/z 576.2494 ([M+Na⁺]), calc. for [C₃₈H₃₅NO₃ +Na⁺] 576.2509; [α]$_D^{29}$=+87.8 (c2.79, CHCl₃); HPLC analysis: Chiralcel OD-H (Hex/IPA=95/5, 0.5 mL/min, 254 nm, 23° C.), 12.1 (major), 14.0 min, 92% ee.

(2R,3S)-tert-Butyl-2-((diphenylmethylene)amino)-3-(naphthalen-2-yl)-5-oxo-5-phenylpentanoate (Compound 6c)

Colorless oil; 93% yield. $^1$H NMR (500 MHz, CDCl₃) δ 7.98 (dd, J=5.1, 3.3 Hz, 2H), 7.74-7.54 (m, 5H), 7.60 (s, 1H), 7.55-7.52 (m, 1H), 7.45-7.30 (m, 9H), 7.22-7.19 (m, 2H), 6.64 (d, J=7.0 Hz, 2H), 4.40-4.37 (m, 1H), 4.29 (d, J=5.0 Hz, 1H), 3.89 (dd, J=17.0, 10.2 Hz, 1H), 3.72 (dd, J=17.0, 3.8 Hz, 1H), 1.31 (s, 9H); $^{13}$C NMR (126 MHz, CDCl₃) δ 198.7, 171.2, 170.0, 141.1, 140.6, 139.4, 137.2, 136.3, 132.8, 130.4, 129.0, 128.9, 128.7, 128.5, 128.4, 128.2, 128.2, 128.1, 127.5, 127.0, 127.0, 126.8, 81.4, 70.9, 44.5, 39.9, 27.9; LRMS (ESI) m/z 576.1 (M+Na⁺), HRMS (ESI) m/z 576.2496 ([M+Na⁺]), calc. for [C₃₈H₃₅NO₃+Na⁺] 576.2509; [α]$_D^{29}$=+44.8 (c 2.74, CHCl₃); HPLC analysis: Chiralcel OD-H (Hex/IPA=95/5, 0.5 mL/min, 210 nm, 23° C.), 12.4 (major), 22.7 min, 90% ee.

(2R,3S)-tert-Butyl-3-([1,1'-biphenyl]-4-yl)-2-((diphenylmethylene)amino)-5-oxo-5-phenylpentanoate (Compound 6d)

Colorless oil; 88% yield. $^1$H NMR (500 MHz, CDCl₃) δ 8.04 -7.94 (m, 2H), 7.72-7.65 (m, 2H), 7.56-7.51 (m, 3H), 7.48-7.34 (m, 10H), 7.30 (t, J=7.4 Hz, 3H), 7.21 (d, J=8.2 Hz, 2H), 6.73 (d, J=7.1 Hz, 2H), 4.26-4.20 (m, 2H), 3.81 (dd, J=17.0, 10.0 Hz, 1H), 3.66 (dd, J=17.0, 3.6 Hz, 1H), 1.34 (s, 9H); $^{13}$C NMR (126 MHz, CDCl₃) δ 198.7, 171.2, 170.0, 141.1, 140.6, 139.4, 137.2, 136.3, 132.8, 130.4, 129.0, 128.9, 128.7, 128.5, 128.4, 128.2, 128.1, 127.5, 127.0, 127.0, 126.8, 81.4, 70.9, 44.5, 39.9, 27.9; LRMS (ESI) m/z 602.1 (M+Na⁺), HRMS (ESI) m/z 602.2664 ([M +Na⁺]), calc. for [C₄₀H₃₇NO₃+Na⁺] 602.2677; [α]$_D^{29}$=+41.0 (c 0.98, CHCl₃); HPLC analysis: Chiralcel OD-H (Hex/IPA=92/8, 0.8 mL/min, 254 nm, 23° C.), 9.4 (major), 13.1 min, 91% ee.

(2R,3S)-tert-Butyl-2-((diphenylmethylene)amino)-3-(4-fluorophenyl)-5-oxo-5-phenylpentanoate (Compound 6e)

Colorless oil; 89% yield. $^1$H NMR (500 MHz, CDCl₃) δ 7.95 (d, J=7.3 Hz, 2H), 7.70-7.66 (m, 2H), 7.54 (t, J=7.4 Hz, 1H), 7.46-7.32 (m, 8H), 7.11 (dd, J=8.6, 5.5 Hz, 2H), 6.86 (t, J=8.7 Hz, 2H), 6.77 (d, J=6.9 Hz, 2H), 4.22-4.09 (m, 2H), 3.69 (dd, J=16.9, 10.0 Hz, 1H), 3.60 (dd, J=16.9, 3.7 Hz, 1H), 1.33 (s, 9H); $^{13}$C NMR (126 MHz, CDCl$_3$) δ 198.6, 171.3, 169.9, 162.6, 160.6, 139.3, 137.1, 136.2, 132.9, 130.5, 130.1, 130.0, 128.8, 128.5, 128.5, 128.3, 128.2, 128.1, 127.5, 115.0, 114.8, 81.4, 70.9, 44.1, 40.2, 27.9; LRMS (ESI) m/z 544.1 (M+Na$^+$), HRMS (ESI) m/z 544.2258 ([M +Na$^+$]), calc. for [C$_{34}$H$_{32}$FNO$_3$+Na$^+$] 544.2258; [α]$_D^{29}$=+ 54.5 (c 1.26, CHCl$_3$); HPLC analysis: Chiralcel OD-H (Hex/IPA=95/5, 0.5 mL/min, 254 nm, 23° C.), 10.2 (major), 19.9 min, 90% ee.

(2R,3S)-tert-Butyl-3-(4-chlorophenyl)-2-((diphenylmethylene)amino)-5-oxo-5-phenylpentanoate (Compound 6l)

Colorless oil; 98% yield. $^1$H NMR (500 MHz, CDCl$_3$) δ 7.99-7.93 (m, 2H), 7.69-7.66 (m, 2H), 7.59-7.51 (m, 1H), 7.46-7.40 (m, 3H), 7.39-7.31 (m, 5H), 7.16-7.12 (m, 2H), 7.11-7.06 (m, 2H), 6.76 (d, J=6.9 Hz, 2H), 4.18-4.14 (m, 2H), 3.73 (dd, J=17.1, 9.7 Hz, 1H), 3.61 (dd, J=17.1, 3.4 Hz, 1H), 1.34 (s, 9H); $^{13}$C NMR (126 MHz, CDCl$_3$) δ 198.4, 171.4, 169.8, 140.1, 139.3, 137.1, 136.2, 133.0, 132.3, 130.5, 129.9, 128.8, 128.5, 128.5, 128.3, 128.2, 128.2, 128.1, 127.5, 81.5, 70.7, 44.1, 39.9, 27.9; LRMS (ESI) m/z 560.0 (M+Na$^+$), HRMS (ESI) m/z 560.1966 ([M +Na$^+$]), calc. for [C$_{34}$H$_{32}$ClNO$_3$+Na$^+$] 560.1963; HPLC analysis: [α]$_D^{29}$=+ 40.9 (c 2.88, CHCl$_3$); Chiralcel OD-H (Hex/IPA=95/5, 0.5 mL/min, 230 nm, 23° C.), 10.1 (major), 16.9 min, 92% ee.

(2R, 3S)-tert-Butyl-3-(4-bromophenyl)-2-((diphenylmethylene)amino)-5-oxo-5-phenylpentanoate (Compound 6g)

Colorless oil; 96% yield. $^1$H NMR (500 MHz, CDCl$_3$) δ 7.99-7.93 (m, 2H), 7.68-7.66 (m, 2H), 7.57-7.53 (m, 1H), 7.47-7.40 (m, 3H), 7.40-7.31 (m, 5H), 7.31-7.27 (m, 2H), 7.06-7.01 (m, 2H), 6.75 (d, J=6.9 Hz, 2H), 4.19-4.10 (m, 2H), 3.79-3.69 (m, 1H), 3.65-3.56 (m, 1H), 1.34 (s, 9H); $^{13}$C NMR (126 MHz, CDCl$_3$) δ 198.4, 171.4, 169. 8, 140.6, 139.2, 137.1, 136.2, 133.0, 131.2, 130.5, 130.3, 128.8, 128.5, 128.4, 128.3, 128.2, 128.1, 127.5, 120.4, 81.6, 70.6, 44.2, 39.7, 27.9; LRMS (ESI) m/z 604.0 (M +Na$^+$), HRMS (ESI) m/z 604.1262 ([M +Na$^+$]), calc. for [C$_{34}$H$_{32}$BrNO$_3$+Na$^+$] 604.1458; [α]$_D^{29}$=+36.7 (c 2.73, CHCl$_3$); HPLC analysis: Chiralcel OD-H (Hex/IPA=95/5, 0.5 mL/min, 230 nm, 23° C.), 10.2 (major), 16.7 min, 92% ee.

(2R, 3S)-tert-Butyl-2-((diphenylmethylene)amino)-3-(4-nitrophenyl)-5-oxo-5-phenylpentanoate (Compound 6h)

Colorless oil; 91% yield. $^1$H NMR (500 MHz, CDCl$_3$) δ 8.05 (m, 2H), 7.97-7.95 (m, 2H), 7.68-7.66 (m, 2H), 7.58-7.55 (m, 1H), 7.48-7.31 (m, 10H), 6.75 (d, J =7.1 Hz, 2H), 4.31-4.27 (m, 1H), 4.20 (d, J=4.8 Hz, 1H), 3.87 (dd, J=17.6, 10.5 Hz, 1H), 3.69 (dd, J=17.6, 3.6 Hz, 1H), 1.36 (s, 9H); $^{13}$C NMR (75 MHz, CDCl$_3$) δ 197.9, 171.9, 169.4, 149.6, 146.6, 138.9, 136.7, 135.9, 133.2, 130.7, 129.4, 128.8, 128.6, 128.4, 128.2, 128.1, 127.3, 123.3, 81.9, 69.9, 44.4, 39.5, 27.9; LRMS (ESI) m/z 571.1 (M +Na$^+$), HRMS (ESI) m/z 571.2187 ([M+Na$^+$]), calc. for [C$_{34}$H$_{32}$N$_2$O$_5$+Na$^+$] 571.2203; [α]$_D^{29}$=+26.1 (c 3.00, CHCl$_3$); HPLC analysis: Chiralcel OD-H (Hex/IPA=92/8, 0.8 mL/min, 230 nm, 23° C.), 8.9 (major), 13.9 min, 94% ee.

(2R,3S)-tert-Butyl-3-(2-chlorophenyl)-2-((diphenylmethylene)amino)-5-oxo-5-phenylpentanoate (Compound 6i)

Colorless oil; 93% yield. $^1$H NMR (500 MHz, CDCl$_3$) δ 8.05-7.98 (m, 2H), 7.69-7.61 (m, 2H), 7.55 (t, J=7.4 Hz, 1H), 7.50-7.42 (m, 2H), 7.42-7.37 (m, 1H), 7.34 (q, J=7.1 Hz, 3H), 7.29-7.23 (m, 3H), 7.18 (dd, J=7.3, 2.0 Hz, 1H), 7.09-7.03 (m, 2H), 6.57 (d, J=6.7 Hz, 2H), 4.73 (dt, J=10.4, 4.0 Hz, 1H), 4.31 (d, J=4.2 Hz, 1H), 3.99 (dd, J=17.3, 10.5 Hz, 1H), 3.70 (dd, J=17.3, 3.9 Hz, 1H), 1.39 (s, 9H); $^{13}$C NMR (126 MHz, CDCl$_3$) δ 198.4, 171.6, 170.0, 139.3, 138.6, 137.1, 136.2, 134.5, 132.9, 130.3, 129.6, 129.2, 128.8, 128.5, 128.4, 128.2, 128.2, 128.0, 127.6, 127.3, 126.3, 81.4, 67.9, 40.7, 38.7, 27.9; LRMS (ESI) m/z 560.1 (M+Na$^+$), HRMS (ESD m/z 560.1962 ([M+Na$^+$]), calc. for [C$_{34}$H$_{32}$ClNO$_3$+Na$^+$] 560.1963; [α]$_D^{29}$=+72.4 (c 2.55, CHCl$_3$); HPLC analysis: Chiralcel OD-H (Hex/IPA=95/5, 0.5 mL/min, 230 nm, 23° C.), 11.0 (major), 13.7 min, 94% ee.

(2R,3S)-tert-Butyl-2-((diphenylmethylene)amino)-3-(4-methoxyphenyl)-5-oxo-5-phenylpentanoate (Compound 6j)

Colorless oil; 89% yield. $^1$H NMR (500 MHz, CDCl$_3$) δ 7.97-7.95 (m, 2H), 7.70-7.68 (m, 2H), 7.54-7.51 (m, 1H), 7.45-7.31(m, 8H), 7.07-7.05 (m, 2H), 6.78 (d, J=6.9 Hz, 2H), 6.72-6.70 (m, 2H), 4.16-4.14 (m, 2H), 3.72 (s, 3H), 3.67-3.63 (m, 1H), 3.60-3.56 (m, 1H), 1.32 (s, 9H); $^{13}$C NMR (126 MHz, CDCl$_3$) δ 198.9, 171.1, 170.1, 158.3, 139.43, 137.3, 136.4, 133.4, 132.8, 130.3, 129.5, 128.5, 128.4, 128.2, 128.2, 128.0, 127.6, 113.5, 81.2, 71.1, 55.2, 44.2, 40.4, 27.9; LRMS (ESD m/z 556.1 (M+Na$^+$), HRMS (ESD m/z 556.2444 ([M+Na$^+$]), calc. for [C$_{35}$H$_{35}$NO$_4$+Na$^+$] 556.2458; [α]$_D^{29}$=+52.7 (c 2.34, CHCl$_3$); HPLC analysis: Chiralcel OD-H (Hex/IPA=90/10, 1.0 mL/min, 254 nm, 23° C.), 5.4 (major), 9.2 min, 85% ee.

(2R,3S)-tert-Butyl-5-(4-chlorophenyl)-2-((diphenylmethylene)amino)-5-oxo-3-phenylpentanoate (Compound 6k)

Colorless oil; 90% yield. $^1$H NMR (500 MHz, CDCl$_3$) δ 7.92-7.90 (m, 2H), 7.68-7.65 (m, 2H), 7.42-7.40 (m, 3H), 7.37-7.29 (m, 5H), 7.18-7.12 (m, 5H), 6.70 (d, J=7.0 Hz, 2H), 4.19-4.15 (m, 2H), 3.71-3.65 (m, 1H), 3.61 (dd, J=16.6, 3.6 Hz, 1H), 1.32 (s, 9H); $^{13}$C NMR (126 MHz, CDCl$_3$) δ 197.6, 171.3, 167.0, 141.3, 139.4, 139.2, 136.3, 135.5, 130.4, 129.7, 128.8, 128.8, 128.5, 128.4, 128.2, 128.2, 128.1, 127.5, 126.7, 81.4, 70.8, 44.9, 40.1, 27.9; LRMS (ESI) m/z 560.1 (M + Na$^+$), HRMS (ESI) m/z 560.1951 ([M+Na$^+$]), calc. for [C$_{34}$H$_{32}$ClNO$_3$+Na$^+$] 560.1963; [α]$_D^{29}$=+44.2 (c 2.12, CHCl$_3$); HPLC analysis: Chiralcel OD-H (Hex/IPA=95/5, 0.5 mL/min, 254 nm, 23° C.), 11.6 (major), 18.1 min, 92% ee.

(2R,3S)-tert-Butyl-2-((diphenylmethylene)amino)-5-(4-nitrophenyl)-5-oxo-3-phenylpentanoate (Compound 6l)

Colorless oil: 91% yield. $^1$H NMR (500 MHz, CDCl$_3$) δ 8.28-8.27 (m, 2H), 8.10-8.08 (m, 2H), 7.66-7.65 (m 2H), 7.42-7.41 (m, 1H), 7.37-7.34 (m, 3H), 7.30 (t, J=7.5 Hz, 2H), 7.18-7.11 (m, 5H), 6.68 (d, J=7.1 Hz, 2H), 4.18-4.14 (m, 2H), 3.78-3.68 (m, 2H), 1.32 (s, 9H); $^{13}$C NMR (126 MHz, CDCl$_3$) δ 197.6, 171.5, 169.9, 150.2, 141.7, 141.0, 139.3, 136.2, 130.5, 129.2, 128.8, 128.5, 128.4, 128.3, 128.2, 128.1, 127.4, 126.8, 123.7, 81.5, 70.6, 44.8, 40.7, 27.9; LRMS (ESI) m/z 571.1 (M+Na⁺), HRMS (ESI) m/z 571.2188 ([M+Na⁺]), calc. for [$C_{34}H_{32}N_2O_5$+Na⁺] 571.2203; $[\alpha]_D^{29}$=+36.5 (c 2.70, CHCl$_3$); HPLC analysis: Chiralcel OD-H (Hex/IPA=92/8, 0.8 mL/min, 210 nm, 23° C.), 12.9 (major), 15.1 min, 91% ee.

(2R, 3S)-tert-Butyl-2-((diphenylmethylene)amino)-5-(4-methoxyphenyl)-5-oxo-3-phenylpentanoate (Compound 6m)

Colorless oil; 83% yield. ¹H NMR (500 MHz, CDCl$_3$) δ 7.96 (d, J=8.8 Hz, 2H), 7.69-7.67 (m, 2H), 7.41-7.30 (m, 6H), 7.15-7.11 (m, 5H), 6.92 (t, J=5.8 Hz, 2H), 6.72 (d, J=6.8 Hz, 2H), 4.21-4.17 (m, 2H), 3.86 (s, 3H), 3.72-3.66 (m, 1H), 3.56-3.52 (m, 1H), 1.32 (s, 9H); ¹³C NMR (126 MHz, CDCl$_3$) δ 197.2, 171.1, 170.1, 163.3, 141.4, 139.4, 136.3, 130.5, 130.4, 130.3, 128.9, 128.6, 128.4, 128.2, 128.1, 128.0, 127.5, 126.5, 113.6, 81.3, 71.0, 55.4, 45.0, 39.7, 27.9; LRMS (ESI) m/z 556.1 (M+Na⁺), HRMS (ESI) m/z 556.2446 ([M+Na⁺]), calc. for [$C_{35}H_{35}NO_4$+Na⁺] 556.2458; $[\alpha]_D^{29}$=+18.0 (c 2.73, CHCl$_3$); HPLC analysis: Chiralcel OD-H (Hex/IPA=90/10, 1.0 mL/min, 254 nm, 23° C.), 6.4 (major), 11.8 min, 87% ee.

(2R,3S)-tert-Butyl-2-((diphenylmethylene)amino)-5-(naphthalen-2-yl)-5-oxo-3-phenylpentanoate (Compound 6n)

Colorless oil; 80% yield. ¹H NMR (500 MHz, CDCl$_3$) δ 8.55 (s, 1H), 8.01-7.98 (m, 2H), 7.86 (d, J=8.4 Hz, 2H), 7.71-7.70 (m, 2H), 7.60-7.54 (m, 2H), 7.42-7.30 (m, 6H), 7.19-7.13 (m, 5H), 6.73 (d, J=6.8 Hz, 2H), 4.29-4.24 (m, 1H), 4.22 (d, J=5.1 Hz, 1H), 3.89 (dd, J=16.7, 10.0 Hz, 1H), 3.76 (dd, J=16.7, 3.9 Hz, 1H), 1.33 (s, 9H); ¹³C NMR (126 MHz, CDCl$_3$) δ 198.7, 171.3, 170.1, 141.4, 139.5, 136.4, 135.5, 134.6, 132.6, 130.3, 129.8, 129.6, 128.9, 128.6, 128.4, 128.3, 128.2, 128.2, 128.1, 127.7, 127.5, 126.6, 126.6, 124.1, 81.3, 71.0, 45.0, 40.1, 27.9; LRMS (ESI) m/z 576.1 (M +Na⁺), HRMS (ESI) m/z 576.2485 ([M +Na⁺]), calc. for [$C_{38}H_{35}NO_3$+Na⁺] 576.2509; $[\alpha]_D^{29}$=+8.0 (c 2.00, CHCl$_3$); HPLC analysis: Chiralcel OD-H (Hex/IPA=90/10, 1.0 mL/min, 210 nm, 23° C.), 5.6 (major), 7.2 min, 91% ee.

(2R,3S)-tert-Butyl-2-((diphenylmethylene)amino)-5-(furan-2-yl)-5-oxo-3-phenyl pentanoate (Compound 6o)

Colorless oil; 95% yield. ¹H NMR (500 MHz, CDCl$_3$) δ 7.68-7.66 (m, 2H), 7.53-7.53 (m, 1H), 7.42-7.29 (m, 6H), 7.17-7.10 (m, 6H), 6.74 (d, J=6.9 Hz, 2H), 6.47 (dd, J=3.5, 1.6 Hz, 1H), 4.21-4.15 (m, 1H), 4.16 (d, J=5.4 Hz, 1H), 3.57 (dd, J=16.3, 9.8 Hz, 1H), 3.42 (dd, J=16.3, 4.2 Hz, 1H), 1.31 (s, 9H); ¹³C NMR (126 MHz, CDCl$_3$) δ 187.8, 171.1, 169.9, 153.0, 146.0, 141.1, 139.4, 136.3, 130.3, 128.9, 128.6, 128.4, 128.2, 128.1, 128.0, 127.6, 126.6, 116.9, 112.1, 81.3, 70.9, 44.7, 40.1, 36.6, 27.8, 24.7; LRMS (ESI) m/z 516.1 (M+Na⁺), HRMS (ESI) m/z 516.2135 ([M+Na⁺]), calc. for [$C_{32}H_{31}NO_4$+Na⁺] 516.2145; $[\alpha]_D^{29}$=+52.1 (c 2.13, CHCl$_3$); HPLC analysis: Chiralcel OD-H (Hex/IPA=90/10, 1.0 mL/min, 254 nm, 23° C.), 6.1 (major), 10.7 min, 90% ee.

(2R,3S)-tert-Butyl-2-((diphenylmethylene)amino)-5-oxo-3-phenyl-5-(thiophen-2-yl)pentanoate (Compound 6p)

Colorless oil; 92% yield. ¹H NMR (500 MHz, CDCl$_3$) δ 7.82 (dd, J=3.8, 1.0 Hz, 1H), 7.69-7.66 (m, 2H), 7.57 (dd, J=4.9, 1.0 Hz, 1H), 7.26-7.42 (m, 6H), 7.18-7.10 (m, 6H), 6.72 (d, J=7.0 Hz, 2H), 4.21-4.16 (m, 2H), 3.66 (dd, J=16.3, 9.6 Hz, 1H), 3.53 (dd, J=16.3, 3.7 Hz, 1H), 1.32 (s, 9H); ¹³C NMR (126 MHz, CDCl$_3$) δ 191.5, 171.2, 170.0, 144.7, 141.1, 139.4, 136.3, 133.3, 131.9, 130.3, 128.9, 128.6, 128.4, 128.2, 128.2, 128.0, 128.0, 127.5, 126.6, 81.4, 70.9, 45.1, 40.8, 27.9; LRMS (ESI) m/z 532.1 (M+Na⁺), HRMS (ESI) m/z 532.1902 ([M+Na⁺]), calc. for [$C_{32}H_{31}NO_3S$+Na] 532.1917; $[\alpha]_D^{29}$=+67.7 (c 2.36, CHCl$_3$); HPLC analysis: Chiralcel OD-H (Hex/IPA=95/5, 0.5 mL/min, 230 nm, 23° C.), 13.3 (major), 35.5 min, 90% ee.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:
1. A compound of formula (I):

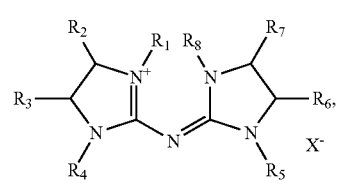

wherein
each of $R_1$ and $R_8$, independently, is $C_1$-$C_{10}$ alkyl, $C_3$-$C_{20}$ cycloalkyl, $C_3$-$C_{20}$ heterocycloalkyl, aryl, or heteroaryl; or $R_1$ and $R_8$ form $C_1$-$C_{10}$ alkyl, $C_3$-$C_{20}$ cycloalkyl, $C_3$-$C_{20}$ heterocycloalkyl, aryl, or heteroaryl;
each of $R_2$, $R_3$, $R_6$, and $R_7$, independently, is H, $C_1$-$C_{10}$ alkyl, $C_3$-$C_{20}$ cycloalkyl, $C_3$-$C_{20}$ heterocycloalkyl, aryl, or heteroaryl; or $R_2$ and $R_3$, together with the two carbon atoms to which they are attached, form $C_4$-$C_{20}$ cycloalkyl, $C_4$-$C_{20}$ heterocycloalkyl, aryl, or heteroaryl; or $R_6$ and $R_7$, together with the two carbon atoms to which they are attached, form $C_4$-$C_{20}$ cycloalkyl, $C_4$-$C_{20}$ heterocycloalkyl, aryl, or heteroaryl;
each of $R_4$ and $R_5$, independently, is $C_1$-$C_{10}$ alkyl, $C_3$-$C_{20}$ cycloalkyl, $C_3$-$C_{20}$ heterocycloalkyl, aryl, or heteroaryl;
$X^-$ is a halide ion, a hydroxide ion, a tetrafluoroboric acid ion, a nitric acid ion, a hexaflorophosphoric acid ion, a tetrakis(3,5-bis(trifluoromethyl)phenyl)boronic acid ion, a sulfuric acid ion, a phosphoric acid ion, a citric acid ion, a methanesulfonic acid ion, a trifluoroacetic acid ion, a malic acid ion, a tartaric acid ion, a fumaric acid ion, a glutamic acid ion, a glucuronic acid ion, a lactic acid ion, a glutaric acid ion, a maleic acid ion, an acetic acid ion, or a p-toluenesulfonic acid ion; and
at least one of the four carbon atoms to which $R_2$, $R_3$, $R_6$, and $R_7$ are attached has an R or S configuration.
2. The compound of claim 1, wherein $R_1$ is identical to $R_8$, $R_2$ is identical to $R_7$, $R_3$ is identical to $R_6$, and $R_4$ is identical to $R_5$.

3. The compound of claim 2, wherein all the carbon atoms to which $R_2$, $R_3$, $R_6$, and $R_7$ are attached have an R or S configuration.

4. The compound of claim 3, wherein all the carbon atoms to which $R_2$, $R_3$, $R_6$, and $R_7$ are attached have an R configuration, or all of them have a S configuration.

5. The compound of claim 4, wherein each of $R_2$, $R_3$, $R_6$, and $R_7$, independently, is aryl or heteroaryl.

6. The compound of claim 4, wherein $R_2$ and $R_3$, together with the two carbon atoms to which they are attached, form $C_4$-$C_{20}$ cycloalkyl; and $R_6$ and $R_7$, together with the two carbon atoms to which they are attached, form $C_4$-$C_{20}$ cycloalkyl.

7. The compound of claim 4, wherein each of $R_1$, $R_4$, $R_5$, and $R_8$, independently, is $C_1$-$C_{10}$ alkyl.

8. The compound of claim 1, wherein the compound is one of Compounds 1a, 1b, 1c, 1d, 1e, and 1f as shown below:

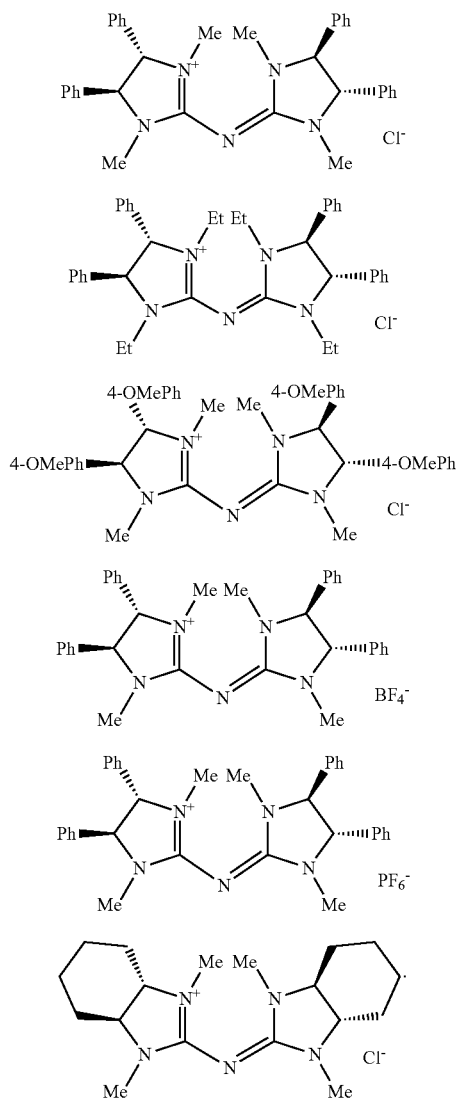

9. The compound of claim 1, wherein $R_1$ is identical to $R_8$, each of $R_2$ and $R_7$ is H, and $R_4$ is identical to $R_5$.

10. The compound of claim 9, wherein all the carbon atoms to which $R_3$ and $R_6$ are attached have an R or S configuration.

11. The compound of claim 10, wherein each of $R_3$ and $R_6$, independently, is aryl or heteroaryl.

12. The compound of claim 10, wherein each of $R_1$, $R_4$, $R_5$, and $R_8$, independently, is $C_1$-$C_{10}$ alkyl.

13. The compound of claim 1, wherein $R_1$ is identical to $R_8$, each of $R_3$ and $R_6$ is H, and $R_4$ is identical to $R_5$.

14. The compound of claim 13, wherein all the carbon atoms to which $R_2$ and $R_7$ are attached have an R or S configuration.

15. The compound of claim 14, wherein each of $R_2$ and $R_7$, independently, is aryl or heteroaryl.

16. The compound of claim 14, wherein each of $R_1$, $R_4$, $R_5$, and $R_8$, independently, is $C_1$-$C_{10}$ alkyl.

17. A method of preparing a compound of formula (I):

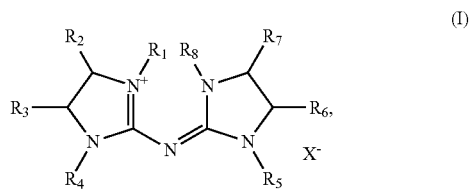

the method comprising:
reacting a compound of formula (II):

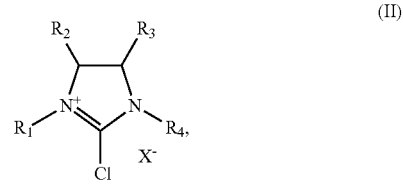

with a compound of formula (III):

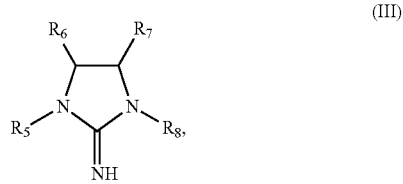

wherein
each of $R_1$ and $R_8$, independently, is $C_1$-$C_{10}$ alkyl, $C_3$-$C_{20}$ cycloalkyl, $C_3$-$C_{20}$ heterocycloalkyl, aryl, or heteroaryl; or $R_1$ and $R_8$ form $C_1$-$C_{10}$ alkyl, $C_3$-$C_{20}$ cycloalkyl, $C_3$-$C_{20}$ heterocycloalkyl, aryl, or heteroaryl;
each of $R_2$, $R_3$, $R_6$, and $R_7$, independently, is H, $C_1$-$C_{10}$ alkyl, $C_3$-$C_{20}$ cycloalkyl, $C_3$-$C_{20}$ heterocycloalkyl, aryl, or heteroaryl; or $R_2$ and $R_3$, together with the two carbon atoms to which they are attached, form $C_4$-$C_{20}$ cycloalkyl, $C_4$-$C_{20}$ heterocycloalkyl, aryl, or heteroaryl; or $R_6$ and $R_7$, together with the two carbon atoms to which they are attached, form $C_4$-$C_{20}$ cycloalkyl, $C_4$-$C_{20}$ heterocycloalkyl, aryl, or heteroaryl;
each of $R_4$ and $R_5$, independently, is $C_1$-$C_{10}$ alkyl, $C_3$-$C_{20}$ cycloalkyl, $C_3$-$C_{20}$ heterocycloalkyl, aryl, or heteroaryl;
$X^-$ is a halide ion, a hydroxide ion, a tetrafluoroboric acid ion, a nitric acid ion, a hexaflorophosphoric acid ion, a tetrakis(3,5-bis(trifluoromethyl)phenyl)boronic acid ion, a sulfuric acid ion, a phosphoric acid ion, a citric acid ion, a methanesulfonic acid ion, a trifluoroacetic acid ion, a malic acid ion, a tartaric acid ion, a fumaric acid ion, a glutamic acid ion, a glucuronic acid ion, a lactic acid ion, a glutaric acid ion, a maleic acid ion, an acetic acid ion, or a p-toluenesulfonic acid ion; and at least one of the four carbon atoms to which $R_2$, $R_3$, $R_6$, and $R_7$ are attached has an R or S configuration.

18. The method of claim 17, wherein the compound of formula (I) is one of Compounds 1a, 1b, 1c, 1d, 1e, and 1f as shown below:

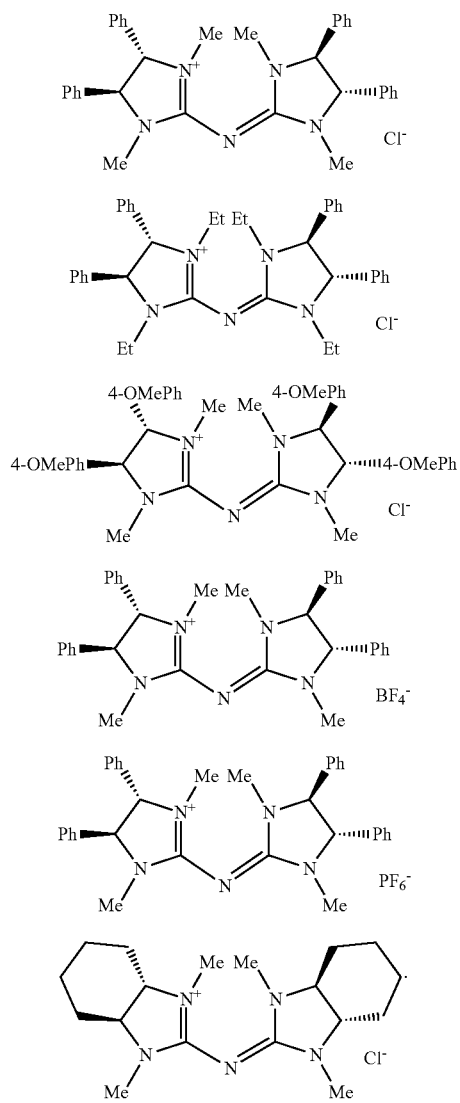

19. A method of preparing a chiral compound of formula (IV):

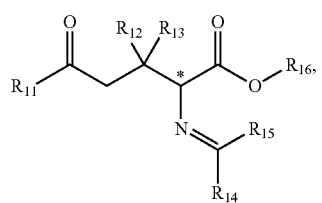

the method comprising:
reacting an enone of formula (V):

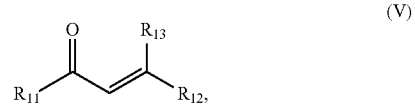

with a Schiff base of formula (VI):

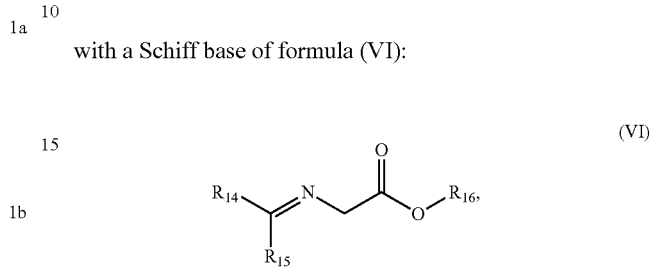

in the presence of a catalyst,
wherein
$R_{11}$ is H, $C_1$-$C_{10}$ alkyl, $C_3$-$C_{20}$ cycloalkyl, $C_3$-$C_{20}$ heterocycloalkyl, aryl, or heteroaryl;

each of $R_{12}$ and $R_{13}$, independently, is H, $C_1$-$C_{10}$ alkyl, $C_3$-$C_{20}$ cycloalkyl, $C_3$-$C_{20}$ heterocycloalkyl, aryl, or heteroaryl; or $R_{12}$ and $R_{13}$, together with the carbon atom to which they are attached, is $C_3$-$C_{20}$ cycloalkyl, or $C_3$-$C_{20}$ heterocycloalkyl;

each of $R_{14}$ and $R_{15}$, independently, is H, $C_1$-$C_{10}$ alkyl, $C_3$-$C_{20}$ cycloalkyl, $C_3$-$C_{20}$ heterocycloalkyl, aryl, or heteroaryl; or $R_{14}$ and $R_{15}$, together with the carbon atom to which they are attached, is $C_3$-$C_{20}$ cycloalkyl, or $C_3$-$C_{20}$ heterocycloalkyl;

$R_{16}$ is $C_1$-$C_{10}$ alkyl, $C_3$-$C_{20}$ cycloalkyl, $C_3$-$C_{20}$ heterocycloalkyl, aryl, or heteroaryl; and the catalyst is a compound of claim 1.

20. The method of claim 19, wherein the catalyst is one of Compounds 1a, 1b, 1c, 1d, 1e, and 1f as shown below:

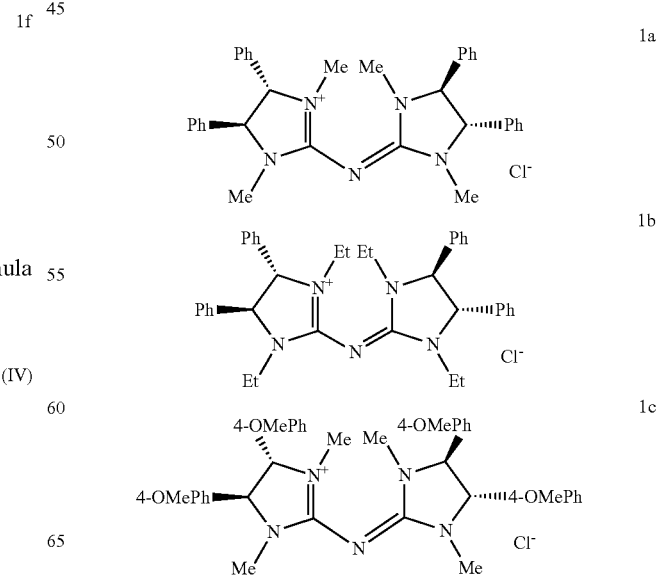

-continued
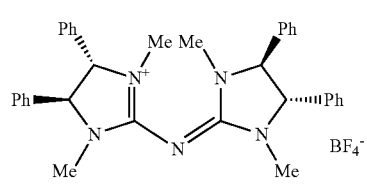
1d
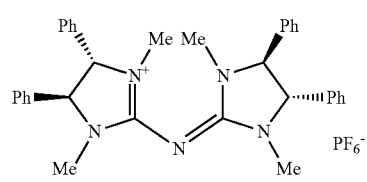
1e
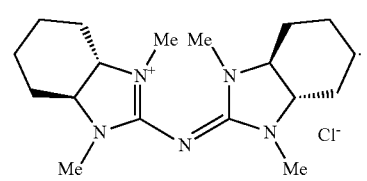
1f
* * * * *